US006407044B2

(12) United States Patent
Dixon

(10) Patent No.: US 6,407,044 B2
(45) Date of Patent: *Jun. 18, 2002

(54) AEROSOL PERSONAL CLEANSING EMULSION COMPOSITIONS WHICH CONTAIN LOW VAPOR PRESSURE PROPELLANTS

(75) Inventor: Thomas Jefferson Dixon, Cincinnati, OH (US)

(73) Assignee: The Proctor & Gamble Company, Cincinnati, OH (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/014,808

(22) Filed: Jan. 28, 1998

(51) Int. Cl.[7] .............................. C11D 3/16; C11D 3/20; C11D 17/04; A61K 7/00; A61K 7/50
(52) U.S. Cl. ..................... 510/140; 510/406; 510/437; 510/507; 510/511; 424/401; 514/846
(58) Field of Search ................. 510/140, 406, 510/437, 507, 511; 424/401; 514/846

(56) References Cited

U.S. PATENT DOCUMENTS

| | | | |
|---|---|---|---|
| 3,028,403 A | 4/1962 | Fritz et al. ................... 260/408 |
| 3,240,794 A | 3/1966 | Bornfleth .................... 260/408 |
| 3,630,949 A | * 12/1971 | Brux et al. ..................... 516/7 |
| 3,852,417 A | 12/1974 | McLaughlin ................. 424/47 |
| 3,923,970 A | 12/1975 | Breuer ......................... 424/47 |
| 3,959,160 A | 5/1976 | Horsler et al. ................ 252/90 |
| 3,970,584 A | * 7/1976 | Hart et al. ................... 510/120 |
| 4,083,954 A | * 4/1978 | Tsuchiya et al. .............. 424/47 |
| 4,145,411 A | 3/1979 | Mende ......................... 424/45 |
| 4,405,489 A | * 9/1983 | Sisbarrd ...................... 424/73 |
| 4,534,959 A | 8/1985 | Schmolka .................... 424/45 |
| 4,686,099 A | 8/1987 | Palinczar ..................... 424/47 |
| 4,705,690 A | 11/1987 | Brand et al. ................. 426/590 |
| 4,705,691 A | 11/1987 | Kupper et al. ............... 426/590 |
| 4,806,262 A | 2/1989 | Snyder ......................... 252/90 |
| 4,871,530 A | * 10/1989 | Grollier et al. ................ 424/47 |
| 4,957,732 A | 9/1990 | Grollier et al. ................ 424/73 |
| 5,002,680 A | 3/1991 | Schmidt et al. ............... 252/90 |
| 5,104,643 A | 4/1992 | Grollier et al. ................ 424/47 |
| 5,160,665 A | * 11/1992 | Owada et al. ............... 252/307 |
| 5,183,707 A | 2/1993 | Herron et al. ............... 428/364 |
| 5,190,563 A | 3/1993 | Herron et al. ................. 8/120 |
| 5,223,244 A | * 6/1993 | Moro et al. ................... 424/46 |
| 5,248,495 A | 9/1993 | Patterson et al. ............. 424/73 |
| 5,262,154 A | 11/1993 | Wendel et al. ................ 424/73 |
| 5,279,819 A | * 1/1994 | Hayes ......................... 424/73 |
| 5,308,526 A | 5/1994 | Dias et al. ................... 252/125 |
| 5,312,559 A | 5/1994 | Kacher et al. .............. 252/125 |
| 5,334,325 A | * 8/1994 | Chaussee .................... 510/120 |
| 5,340,492 A | 8/1994 | Kacher et al. .............. 252/112 |
| 5,429,815 A | 7/1995 | Faryniarz et al. ............. 424/47 |
| 5,560,859 A | * 10/1996 | Hartmann et al. .......... 510/135 |
| 5,602,091 A | * 2/1997 | Monson et al. ............. 510/406 |
| 5,635,469 A | 6/1997 | Fowler et al. ............... 510/406 |
| 5,650,384 A | 7/1997 | Gordon et al. .............. 510/159 |
| 5,674,511 A | * 10/1997 | Kacher et al. .............. 424/401 |
| 5,716,920 A | * 2/1998 | Glenn, Jr. et al. .......... 510/159 |
| 5,753,210 A | * 5/1998 | McEleney et al. ............ 424/59 |
| 5,869,070 A | * 2/1999 | Dixon et al. ................ 424/401 |
| 5,885,948 A | * 3/1999 | Glenn, Jr. et al. .......... 510/130 |
| 5,902,225 A | * 5/1999 | Monson ....................... 516/10 |
| 5,932,528 A | * 8/1999 | Glenn, Jr. et al. .......... 510/130 |
| 6,066,608 A | * 5/2000 | Glenn, Jr. et al. .......... 510/159 |

FOREIGN PATENT DOCUMENTS

| | | | |
|---|---|---|---|
| EP | 0 194 097 A1 | 9/1986 | ............ A61K/7/50 |
| GB | 2 291 805 | 2/1996 | ............ A61K/7/32 |
| WO | 9513349 | * 5/1995 | |
| WO | WO 96/25144 | 8/1996 | ............ A61K/7/48 |

* cited by examiner

*Primary Examiner*—Lorna M. Douyon
(74) *Attorney, Agent, or Firm*—Tara M. Rosnell; Stephen T. Murphy

(57) ABSTRACT

An aerosol personal cleansing composition comprising from about 85% to about 95% of a neat cleansing lotion comprising from about 0.5% to about 30%, by weight of the neat cleansing lotion, of a lathering surfactant, from about 0.5% to about 40%, by weight of the neat cleansing lotion, of a lipophilic skin moisturizing agent, from about 0.1% to about 10% by weight of the neat cleansing lotion, of a stabilizer, and from about 35% to about 90%, by weight of the neat cleansing lotion, of water; and from about 3% to about 15% of a hydrocarbon propellant having a vapor pressure of from about 3 psig to about 15 psig.

20 Claims, No Drawings

AEROSOL PERSONAL CLEANSING EMULSION COMPOSITIONS WHICH CONTAIN LOW VAPOR PRESSURE PROPELLANTS

TECHNICAL FIELD

The present invention relates to aerosol personal cleansing compositions which provide improved moisturization of the skin. The aerosol personal cleansing compositions of the present invention contain a lipophilic skin moisturizing agent, a surfactant, a stabilizer, water, and a hydrocarbon propellant with a low vapor pressure. The compositions of the invention increase the deposition of the moisturizing agent and increases the lather of the personal cleansing composition. The low vapor pressure propellant also gives the product the appearance of a lotion product.

BACKGROUND OF THE INVENTION

Moisturizing personal cleansing compositions are popular in the United States and around the world. Desirable moisturizing personal cleansing compositions must meet a number of criteria. For example, in order to be acceptable to consumers, a moisturizing personal cleansing product must exhibit good cleaning properties, must exhibit good lathering characteristics, must be mild to the skin (not cause drying or irritation) and preferably should even provide a moisturization benefit to the skin.

Moisturizing personal cleansing products which contain high levels of lipophilic skin conditioning agents have been disclosed. U.S. Pat. No. 5,650,384, issued to Gordon et al., on Jul. 22, 1997 discloses the use of such a cleansing product used in conjunction with a mesh bath sponge. The mesh sponge provides enhanced lathering for the cleansing system.

Aerosol personal skin cleansers are also well known. U.S. Pat. No. 5,002,680, issued to Schmidt et al., on Mar. 26, 1991 discloses mild skin cleansing, aerosol mousses containing lipophilic moisturizing agents. The compositions taught in Schmidt deliver low levels of moisturizing agent deposition to the skin. Also, typical aerosol cleansing products are dispensed from the package as a foam. Some consumers prefer the aesthetic characteristics of a lotion product over a foam.

The skin feel attributes that result from skin conditioning agents being deposited on the skin is enormously popular with consumers. Although products such as Oil of Olay Moisturizing Body Wash ®, which deposit lipophilic skin moisturizing agents on the skin are very popular with consumers, some consumers would prefer to have an even greater moisturizing benefit delivered from these personal cleansing products without loosing product cleansing and lathering characteristics. Therefore, it would be desirable to provide a personal cleansing composition which dispenses from its package as a lotion and has improved moisturization properties.

It has now been found that the deposition of the moisturizing phase of the personal cleansing composition on the skin can be increased by using a hydrocarbon propellant which has a low vapor pressure. The use of low vapor pressure propellants also results in an aerosol product that is delivered with the appearance of a lotion product.

SUMMARY OF THE INVENTION

The present invention relates to an aerosol personal cleansing composition comprising from about 85% to about 95% of a neat cleansing lotion comprising i) from about 0.5% to about 30%, by weight of the neat cleansing lotion, of a lathering surfactant, ii) from about 0.5% to about 40%, by weight of the neat cleansing lotion, of a lipophilic skin moisturizing agent, iii) from about 0.1% to about 2% by weight of the neat cleansing lotion, of a stabilizer, and iv) from about 35% to about 90%, by weight of the neat cleansing lotion, of water; and from about 3% to about 15% of a hydrocarbon propellant having a vapor pressure of from about 3 psig to about 15 psig.

DETAILED DESCRIPTION OF THE INVENTION

The present invention relates to aerosol personal cleansing compositions which provide improved moisturization to the skin. As used herein, "personal cleansing compositions" refers to rinse-off personal cleansing products, including, but not limited to, shower washes, liquid handsoaps, facial cleansers, and shampoos. As used herein, the term "aerosol" refers to a product wherein the neat personal cleansing composition is packaged in a container, along with a propellant gas. "Neat", as used herein, describes the personal cleansing composition before it is packaged with the propellant. The aerosol compositions of the present invention form a lotion, rather than a foam, after being dispensed from the package. The use of low vapor pressure hydrocarbon propellants in the present invention results in increased deposition of the moisturizing personal cleansing compositions of the present invention. Without being limited by theory it is believed that since hydrocarbon compounds are more soluble in the lipophilic skin moisturizing agent, than non-hydrocarbon compounds, some of the hydrocarbon propellants are solubilized in the lipophilic skin moisturizing agent, changing the rheology of the agent. The hydrocarbon appears to make the high viscosity moisturizing agent more spreadable, which increases the deposition of the agent. When low vapor pressure hydrocarbon propellants are solubilized in the moisturizing agent in a aqueous surfactant matrix, it has been found that a distinct highly concentrated lamellar phase crystalline structure is formed which results in a further increase in deposition of the moisturizing agent.

The aerosol personal cleansing compositions of the present invention contain a lathering surfactant, a lipophilic skin moisturizing agent, a stabilizer, water and a low vapor pressure propellant. The personal cleansing compositions are preferably emulsions which are made up of a moisturizing phase and an aqueous cleansing phase. The aerosol personal cleansing compositions are described in detail as follows.

I. Ingredients

A. Lipophilic Skin Moisturizing Agent

The aerosol personal cleansing compositions of the present invention comprise from about 0.5% to about 40%, preferably from about 3% to about 30%, more preferably from about 5% to about 25%, by weight of the composition, of a lipophilic skin moisturizing agent.

The lipophilic skin moisturizing agents suitable for use herein typically have a consistency (k) which ranges from about 0.01 poise to about 1000 poise, preferably from about 100 poise to about 1000 poise, more preferably from about 200 poise to about 800 poise, and most preferably from about 400 poise to about 500 poise, as measured by the Viscosity Method for Lipophilic Skin Moisturizing Agents hereinafter set forth in the Analytical Methods section.

In some cases, the lipophilic skin moisturizing agent can also desirably be defined in terms of its solubility parameter, as defined by *Vaughan in Cosmetics and Toiletries*, Vol. 103, p. 47–69, October 1988. A lipophilic skin moisturizing agent having a Vaughan solubility Parameter (VSP) of from 5 to 10, preferably from 5.5 to 9 is suitable for use in the moisturizing personal cleansing compositions herein.

A wide variety of lipid type materials and mixtures of materials are suitable for use as the lipophilic skin moisturizing agents in the personal cleansing compositions of the present invention. Preferably, the lipophilic skin conditioning agent is selected from the group consisting of hydrocarbon oils and waxes, silicones, fatty acid derivatives, cholesterol, cholesterol derivatives, di- and tri-glycerides, vegetable oils, vegetable oil derivatives, liquid nondigestible oils such as those described in U.S. Pat. No. 3,600,186 to Mattson; Issued Aug. 17, 1971 and 4,005,195 and 4,005,196 to Jandacek et al; both issued Jan. 25, 1977, all of which are herein incorporated by reference, or blends of liquid digestible or nondigestible oils with solid polyol polyesters such as those described in U.S. Pat. No. 4,797,300 to Jandacek; issued Jan. 10, 1989; U.S. Pat. Nos. 5,306,514, 5,306,516 and 5,306,515 to Letton; all issued Apr. 26, 1994, all of which are herein incorporated by reference, and acetoglyceride esters, alkyl esters, alkenyl esters, lanolin and its derivatives, milk-tri-glycerides, wax esters, beeswax derivatives, sterols, phospholipids and mixtures thereof. Fatty acids, fatty acid soaps and water soluble polyols are specifically excluded from our definition of a lipophilic skin moisturizing agent.

Hydrocarbon oils and waxes: Some examples are petrolatum, mineral oil micro-crystalline waxes, polyalkenes (e.g. hydrogenated and nonhydrogenated polybutene and polydecene), paraffins, cerasin, ozokerite, polyethylene and perhydrosqualene. Blends of petrolatum and hydrogenated and nonhydrogenated high molecular weight polybutenes wherein the ratio of petrolatum to polybutene ranges from about 90:10 to about 40:60 are also suitable for use as the lipid skin moisturizing agent in the compositions herein.

Silicone Oils: Some examples are dimethicone copolyol, dimethylpolysiloxane, diethylpolysiloxane, high molecular weight dimethicone, mixed C1–C30 alkyl polysiloxane, phenyl dimethicone, dimethiconol, and mixtures thereof. More preferred are non-volatile silicones selected from dimethicone, dimethiconol, mixed C1–C30 alkyl polysiloxane, and mixtures thereof. Nonlimiting examples of silicones useful herein are described in U.S. Pat. No. 5,011,681, to Ciotti et al., issued Apr. 30, 1991, which is incorporated by reference.

Di- and tri-glycerides: Some examples are castor oil, soy bean oil, derivatized soybean oils such as maleated soy bean oil, safflower oil, cotton seed oil, corn oil, walnut oil, peanut oil, olive oil, cod liver oil, almond oil, avocado oil, palm oil and sesame oil, vegetable oils and vegetable oil derivatives; coconut oil and derivatized coconut oil, cottonseed oil and derivatized cottonseed oil, jojoba oil, cocoa butter, and the like.

Acetotlyceride esters are used and an example is acetylated monoglycerides.

Lanolin and its derivatives are preferred and some examples are lanolin, lanolin oil, lanolin wax, lanolin alcohols, lanolin fatty acids, isopropyl lanolate, acetylated lanolin, acetylated lanolin alcohols, lanolin alcohol linoleate, lanolin alcohol riconoleate.

It is most preferred when at least 75% of the lipophilic skin conditioning agent is comprised of lipids selected from the group consisting: petrolatum, blends of petrolatum and high molecular weight polybutene, mineral oil, liquid nondigestible oils (e.g. liquid cottonseed sucrose octaesters) or blends of liquid digestible or nondigestible oils with solid polyol polyesters (e.g. sucrose octaesters prepared from C22 fatty acids) wherein the ratio of liquid digestible or nondigestible oil to solid polyol polyester ranges from about 96:4 to about 80:20, hydrogenated or nonhydrogenated polybutene, micro-crystalline wax, polyalkene, paraffin, cerasin, ozokerite, polyethylene, perhydrosqualene, dimethicones, alkyl siloxane, polymethylsiloxane, methylphenylpolysiloxane and mixtures thereof. When as blend of petrolatum and other lipids is used, the ratio of petrolatum to the other selected lipids (hydrogenated or unhydrogenated polybutene or polydecene or mineral oil) is preferably from about 10:1 to about 1:2, more preferably from about 5:1 to about 1:1.

Preferred embodiments of the neat cleansing lotions of the aerosol personal cleansing compositions of the present invention are emulsions which comprise a moisturizing phase. The moisturizing phase provides the vehicle for delivering the lipophilic skin moisturizing agents to the skin of the user.

The average droplet size of the moisturizing phase droplets, which comprise the lipophilic skin moisturizing agent, ranges from about 0.005 microns to about 1000 microns, preferably from about 0.1 to about 500 microns, more preferably from about 10 to about 350 microns, and most preferably from about 50 to about 200 microns in diameter. See U.S. Pat. No. Re. 34,584, Grote et al., Reissued Apr. 12, 1994, U.S. Pat. No. 5,246,694, issued to Birtwistle, on Sep. 21, 1993, and U.S. Pat. No. 5,650,84, issued to Gordon et al., on Jul. 22, 1997, all herein incorporated by reference. For purposes of the present invention, the diameter of a droplet means the longest length of the droplet. The droplet size is measured using the Droplet Size Measurement for Moisturizing Phase Droplets Method, hereinafter set forth in the Analytical Methods Section.

B. Stabilizer

The aerosol personal cleansing compositions of the present invention also typically contain from about 0.1% to about 10%, preferably from about 0.25% to about 8%, more preferably from about 0.5% to about 5%, and most preferably from about 0.5% to about 1% of a stabilizer.

The stabilizer is used to form a crystalline stabilizing network in the composition that prevents the lipophilic skin moisturizer agent droplets from coalescing and phase splitting in the product. The network exhibits time dependent recovery of viscosity after shearing (e.g., thixotropy).

The stabilizers used herein are not surfactants. The stabilizers provide improved shelf and stress stability, but allow the oil-in-water emulsion to separate upon lathering, and thereby provide for increased lipid deposition onto the skin. This is particularly true when the oil-in-water cleansing emulsions of the present invention are used in conjunction with a polymeric diamond meshed sponge implement such as that described in Campagnoli; U.S. Pat. No. 5,144,744; Issued Sep. 8, 1992, herein incorporated by reference. In one embodiment of the present invention, the stabilizer employed in the personal cleansing compositions herein comprises a crystalline, hydroxyl-containing stabilizer. This stabilizer can be a hydroxyl-containing fatty acid, fatty ester or fatty soap water-insoluble wax-like substance or the like.

The crystalline, hydroxycontaining stabilizer is selected from the group consisting of:

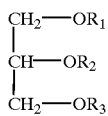

wherein

R$_2$ is R$_1$ or H
R$_3$ is R$_1$ or H
R$_4$ is C$_{0-20}$ Alkyl
R$_5$ is C$_{0-20}$ Alkyl,
R$_6$ is C$_{0-20}$ Alkyl
R$_4$+R$_5$+R$_6$=C$_{10-22}$
and wherein $1 \leq x+y \leq 4$;

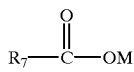

wherein
R$_7$ is —R$_4$(CHOH)$_x$R$_5$(CHOH)$_y$R$_6$
M is Na$^+$, K$^+$ or Mg$^{++}$, or H; and
iii) mixtures thereof;

Some preferred hydroxyl-containing stabilizers include 12-hydroxystearic acid, 9,10-dihydroxystearic acid, tri-9,10-dihydroxystearin and tri-12-hydroxystearin (hydrogenated castor oil is mostly tri-12-hydroxystearin). Tri-12-hydroxystearin is most preferred for use in the emulsion compositions herein.

When these crystalline, hydroxyl-containing stabilizers are utilized in the personal cleansing compositions herein, they are typically present at from about 0.5% to 10%, preferably from 0.75% to 8%, more preferably from 1.25% to about 5% of the aerosol personal cleansing compositions. The stabilizer is insoluble in water under ambient to near ambient conditions.

Alternatively, the stabilizer employed in the personal cleansing compositions herein can comprise a polymeric thickener. When polymeric thickeners as the stabilizer in the personal cleansing compositions herein, they are typically included in an amount ranging from about 0.01% to about 5%, preferably from about 0.3% to about 3%, by weight of the composition. The polymeric thickener is preferably an anionic, nonionic, cationic or hydrophobically modifier polymer selected from the group consisting of cationic polysaccharides of the cationic guar gum class with molecular weights of 1,000 to 3,000,000; anionic, cationic, and nonionic homopolymers derived from acrylic and/or methacrylic acid; anionic, cationic, and nonionic cellulose resins; cationic copolymers of dimethyldialkylammonium chloride, and acrylic acid; cationic homopolymers of dimethylalkylammonium chloride; cationic polyalkylene and ethoxypolyalkylene imines; polyethylene glycol of molecular weight from 100,000 to 4,000,000; and mixtures thereof Preferably, the polymer is selected from the group consisting of Sodium Polyacrylate, Hydroxy Ethyl Cellulose, Cetyl Hydroxy Ethyl Cellulose, and Polyquaternuium 10.

Another stabilizer which can be employed in the neat cleansing lotions herein are C10–C22 ethylene glycol fatty acid ester. C10–C22 ethylene glycol fatty acid esters can also desirably be employed in combination with the polymeric thickeners hereinbefore described. The ester is preferably a diester, more preferably a C14–C18 diester, most preferably ethylene glycol distearate. When C10–C22 ethylene glycol fatty acid esters are utilized as the stabilizer in the neat cleansing lotions herein, they are typically present at from about 3% to about 10%, preferably from about 5% to about 8%, more preferably from about 6% to about 8% of the cleansing compositions.

Another class of stabilizer which can be employed in the neat cleansing lotions of the present invention comprises dispersed amorphous silica selected from the group consisting of fumed silica and precipitated silica and mixtures thereof. As used herein the term "dispersed amorphous silica" refers to small, finely divided non-crystalline silica having a mean agglomerate particle size of less than about 100 microns.

Fumed silica, which is also known as arced silica, is produced by the vapor phase hydrolysis of silicon tetrachloride in a hydrogen oxygen flame. It is believed that the combustion process creates silicone dioxide molecules which condense to form particles. The particles collide, attach and sinter together. The result of this process is a three dimensional branched chain aggregate. Once the aggregate cools below the fusion point of silica, which is about 1710° C., further collisions result in mechanical entanglement of the chains to form agglomerates. Precipitated silicas and silica gels are generally made in aqueous solution. See, Cabot Technical Data Pamphlet TD-100 entitled "CAB-O-SIL® Untreated Fumed Silica Properties and Functions", October 1993, and Cabot Technical Data Pamphlet TD-104 entitled "CAB-O-SIL® Fumed Silica in Cosmetic and Personal Care Products", March 1992, both of which are herein incorporated by reference. The fumed silica preferably has a mean agglomerate particle size ranging from about 0.1 microns to about 100 microns, preferably from about 1 micron to about 50 microns, and more preferably from about 10 microns to about 30 microns. The agglomerates are composed of aggregates which have a mean particle size ranging from about 0.01 microns to about 15 microns, preferably from about 0.05 microns to about 10 microns, more preferably from about 0.1 microns to about 5 microns and most preferably from about 0.2 microns to about 0.3 microns. The silica preferably has a surface area greater than 50 sq. m/gram, more preferably greater than about 130 sq. m./gram, most preferably greater than about 180 sq. m./gram.

When amorphous silicas are used as the stabilizer herein, they are typically included in the emulsion compositions at levels ranging from about 0.1% to about 10%, preferably from about 0.25% to about 8%, more preferably from about 0.5% to about 5%.

A fourth class of stabilizer which can be employed in the aerosol cleansing compositions of the present invention comprises dispersed smectite clay selected from the group consisting of bentonite and hectorite and mixtures thereof. Bentonite is a colloidal aluminum clay sulfate. See Merck Index, Eleventh Edition, 1989, entry 1062, p. 164, which is incorporated by reference. Hectorite is a clay containing sodium, magnesium, lithium, silicon, oxygen, hydrogen and fluorine. See Merck Index, eleventh Edition, 1989, entry 4538, p. 729, which is herein incorporated by reference.

C. The Lathering Surfactant

The neat cleansing lotions of the present invention also comprise a lathering surfactant selected from the group consisting of anionic surfactants, nonionic surfactants, cationic surfactants, amphoteric surfactants, and mixtures thereof.

The lathering surfactant is defined herein as a surfactant or surfactant mixture thereof that when combined have an equilibrium surface tension of between 15 and 50 dynes/cm, more preferably between 25 and 40 dynes/cm as measured at the CMC (critical micelle concentration) at 25° C. Some surfactant mixes can have a surface tension lower than those of its individual components.

The neat cleansing lotions herein comprise from about 0.5% to about 30%, preferably from about 2% to about 20%, and most preferably from about 5% to about 10% of a lathering surfactant.

Anionic surfactants useful herein include: acyl isethionates, acyl sarcosinates, alkylglycerylether sulfonates, alkyl sulfates, acyl lactylate, methylacyl taurates, paraffin sulfonates, linear alkyl benzene sulfonates, N-acyl glutamates, alkyl sulfosuccinates, alpha sulfo fatty acid esters, alkyl ether carboxylates, alkyl phosphate esters, ethoxylated alkyl phosphate esters, alpha olefin sulphates, the alkyl ether sulfates (with 1 to 12 ethoxy groups) and mixtures thereof, wherein said surfactants contain C8 to C22 alkyl chains and wherein the counterion is selected from the group consisting of Na, K, $NH_4$, $N(CH_2CH_2OH)_3$. The anionic surfactant is more preferred when selected from the group consisting of acyl isethionate, acyl sarcosinates, acyl lactylates, alkyl sulfosuccinates, alkylglycerylether sulfonates, methylacyl taurates, alkyl ether sulfates, alkyl sulfates, alkyl phosphate esters and mixtures thereof, wherein said surfactants contain has C8 to C14 alkyl chains and is present at a level of from about 8% to about 20%.

Amphoteric synthetic surfactants cannot serve as the sole surfactant in this product, but are preferred as a co-surfactant at a lower level of from about 1 part to about 10 parts, by weight and the more preferred types are selected from alkyl-ampho mono- and di-acetates, alkyl betaines, alkyl dimethyl amine oxides, alkyl sultaines, alkyl amidopropyl betaines, alkyl amidopropyl hydroxysultaines, and mixtures thereof, wherein said surfactants contain C8 to C22 alkyl chains.

Nonionic synthetic surfactant cannot serve as the sole surfactant in this product, but can be used as a co-surfactant at a lower level of from about 1% to about 15% by weight. The more preferred types selected from the group consisting: alkyl glucose amides, alkyl glucose esters, polyoxyethylene amides, fatty alkane amides, alkyl amine oxides, alkyl polyglucosides, polyoxyethylene alkyl phenols, polyoxyethylene esters of fatty acids, EO/PO block co-polymers such as polyoxamines and poloxamers, sorbitan esters and alcohol esters, and mixtures thereof.

Cationic synthetic surfactant cannot serve as the sole surfactant in this product, but are preferred as a co-surfactant at a lower level of from about 0.5% to about 6%, by weight. The more preferred types of cationic surfactants are selected from the group consisting: alkyl trimonium chloride and methylsulfate, and dialkyldimonium chloride and methylsulfate, and alkyl alkonium chloride and methylsulfate and mixtures thereof. These surfactants contain C12 to C24 carbon atoms per alkyl chain. The most preferred cationic is selected from the group consisting of stearylalkonium chloride, stearyltrimonium chloride, Di-stearyldimonium chloride, and mixtures thereof. Cationic surfactants may also act as a lipid deposition aid.

The neat cleansing lotions herein can also optionally contain C8–C14 fatty acid soap; where the soap has a counterion selected from the group consisting of K and N(CH2CH2OH)$_3$, and mixtures thereof, in addition to the lathering synthetic surfactant. In one preferred embodiment of the present invention, the aerosol personal cleansing compositions comprise less than about 5%, preferably less than about 4%, more preferably less than about 3%, and most preferably less than about 2% by weight of fatty acid soap.

D. Water

The aerosol personal cleansing emulsion compositions of the present invention comprise water as an essential component. The water is typically present at a level of from about 50% to about 90%, preferably from about 60% to about 85%, and most preferably from about 65% to about 75% of the neat cleansing lotions of the present invention.

The neat cleansing lotions of the present invention also comprise an aqueous cleansing phase which comprises a stabilizer, a lathering surfactant, and water. Each of these is described in detail as follows:

E. Low Vapor Pressure Hydrocarbon Propellant

The aerosol personal cleansing compositions of the present invention comprise a low vapor pressure gas propellant. Low vapor pressure hydrocarbon propellants have a vapor pressure from about 3 psig to about 15 psig at 70° F. The low vapor pressure hydrocarbon propellant is used at levels from about 3% to about 15%, and preferably from about 5% to about 12% of the aerosol personal cleansing composition. The low vapor pressure hydrocarbon propellant is selected from the group consisting of isobutane, n-pentane, isopentane, and hexane, and mixtures thereof. The propellant must comprise less than about 15%, preferably less than 10% and more preferably less than 5%, by weight of the propellant, of non-hydrocarbon propellants. The class of non-hydrocarbon propellants includes carbon dioxide, nitrous oxide (especially $N_2O$), flourochlorohydrocarbons, and mixtures thereof. A preferred propellant for the present invention comprises a mixture 85% isopentane and 15% isobutane. Low vapor pressure propellants have been found to increase the deposition of the lipophilic skin moisturizing agent over higher vapor pressure hydrocarbon propellants. With out being limited by theory, it is believed that the moisturizing agent with solubilized low vapor pressure hydrocarbon propellants in a aqueous surfactant matrix, form a distinct lamellar phase crystal structure which results in a further increase in deposition of the moisturizing agent.

The composition is packed in a valved container that is designed to maintain the composition under pressure and to dispense it upon opening of the valve. Such valves and containers are well known and valves of this general type are disclosed, by way of example and without limitation, in prior U.S. Pat. Nos. 5,248,495 dated Sep. 28, 1993; 2,772,820 dated Dec. 4, 1956; 2,777,735 dated Jan. 15, 1957; 3,191,816 dated Jun. 29, 1965; 3,348,743 dated Oct. 24, 1967; 3,540,624 dated Nov. 17, 1970. The moisturizing product of the present invention comprises a sealed container, such as an essentially cylindrical bottle, having a dispensing means such as a nozzle. The container contains the composition and propellant gas. Suitable containers may be made from any material, especially aluminum, tin-plate, plastics including PET, OPP, PE or polyamide and including mixtures, laminates or other combinations of these. Foam is dispensed when the nozzle is activated and the cleansing composition is released together with the propellant gas. The propellant gas expands to form many "bubbles" within the composition thereby creating the foam.

F. Optional Ingredients

The personal cleansing compositions of the present invention can also contain a number of optional ingredients in the aqueous phase.

Weighting Oil

Weighting oils can optionally be added to the lipophilic skin moisturizing agent to increase the specific gravity of the agent, which allows for the improved deposition of moisturizing agent out of an emulsion composition with lower particle size droplets. The moisturizing phase of emulsion embodiments of the moisturizing personal cleansing compositions of the present invention may contain from about 1% to about 20%, preferably from about 3% to about 15%, and more preferably from about 5% to about 10%, by weight of the composition, of a weighting oil. When weighting oils are used, the ratio of the lipophilic skin moisturizing agent to the weighting oil is critical to achieving the deposition benefits of the present invention and must range from about 20:1 to about 1:10, preferably from about 10:1 to about 1:5, and more preferably from about 5:1 to about 1:1.

The weighting oils suitable herein typically have a specific gravity of from about 0.9 to about 2.0, preferably from about 1.1 to about 1.7, and more preferably from about 1.2 to about 1.5.

Specific examples of suitable weighting oils are disclosed in U.S. Pat. No. 3,028,403, issued to Fritz et al., on Apr. 3, 1962, U.S. Pat. No. 3,240,794, issued to Bornfleth, on Mar. 15, 1966, U.S. Pat. No. 4,705,690, issued to Brand et al., on Nov. 10, 1987, and U.S. Pat. No. 4,705,691, issued to Kupper, on Nov. 10, 1987, all incorporated by reference herein. Suitable weighting oils can be selected from the group consisting of brominated esters of long chain fatty acids, brominated fatty alcohols, brominated ketones, brominated amides, brominated nitrites, brominated sulfonated fats, brominated hydrocarbons, brominated liquid polyol polyesters, glycerol ester of wood rosin (ester gum rosin), sucrose acetate isobutyrate (SAIB), gum damar, colophony, gum elemi, and mixtures thereof. Preferred weighting oils are selected from the group consisting of brominated vegetable oil, brominated polyol fatty acid polyester, glycerol ester of wood rosin and mixtures thereof. Most preferred is brominated vegetable oil.

Other Optional Ingredients

The moisturizing personal cleansing compositions of the present invention can optionally include water-dispersible, gel-forming polymers. This polymer is preferably an anionic, nonionic, cationic or hydrophobically modified polymer, selected from the group consisting of cationic polysaccharides of the cationic guar gum class with molecular weights of 1,000 to 3,000,000, anionic, cationic and nonionic homopolymers derived from acrylic and/or methacrylic acid, anionic, cationic and nonionic cellulose resins; cationic copolymers of dimethyldialkylammonium chloride and acrylic acid; cationic homopolymers of dimethyldialkylammonium chloride; cationic polyalkylene and ethoxypolyalkylene imines polyethylene glycol of molecular weight from 100,00 to 4,000,000; and mixtures thereof. Preferably, the polymer is selected form the group consisting of Sodium Polyacrylate, Hydroxy Ethyl Cellulose, Cetyl Hydroxy Ethyl Cellulose, and Polyquaternium 10.

The polymer is preferably included in the compositions of the present invention at a level of from about 0.1 parts to 1 part, more preferably 0.1 parts to 0.5 parts. The polymers can improve the sensory feel of the lipid on skin in addition to providing product stabilization. The improved sensory feel results from reduced tackiness and greasiness and improved smoothness. It is an especially preferred embodiment to use mixture of polymers, some of which are preferred for product stabilization, some are preferred for improved sensory feel. Preferred polymers to improve sensory feel are selected from the group consisting: of polyethylene glycol, hydroxypropyl guar, guar hydroxypropyltrimonium chloride, polyquaternary 3, 5, 6, 7, 10, 11 and 24 and mixtures thereof.

Another highly preferred optional component of the present compositions are one or more humectants and solutes. A variety of humectants and solutes can be employed and can be present at a level of from about 0.5% to about 30%, more preferably from about 3.0% to about 20%. The humectants and solutes are non-volatile, organic materials having a solubility of a least 5 parts in 10 parts water. A preferred water soluble, organic material is selected from the group consisting of a polyol of the structure:

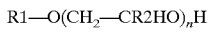

where R1=H, C1–C4 alkyl; R2=H, $CH_3$ and n=1–200; C2–C10 alkane diols; guanidine; glycolic acid and glycolate salts (e.g. ammonium and quaternary alkyl ammonium); lactic acid and lactate salts (e.g. ammonium and quaternary alkyl ammonium); polyhydroxy alcohols such as sorbitol, glycerol, hexanetriol, propylene glycol, hexylene glycol and the like; polyethylene glycol; sugars and starches; sugar and starch derivatives (e.g. alkoxylated glucose); panthenol (including D-, L-, and the D, L- forms); pyrrolidone carboxylic acid; hyaluronic acid; lactamide monoethanolamine; acetamide monoethanolamine; urea; and ethanolamines of the general structure $(HOCH_2CH_2)_xNH_y$ where x=1–3; y=0–2, and x+y=3, and mixtures thereof. The most preferred polyols are selected from the group consisting of glycerin, polyoxypropylene(1) glycerol and polyoxypropylene(3) glycerol, sorbitol, butylene glycol, propylene glycol, sucrose, urea and triethanolamine.

Preferred water soluble organic material are selected from the group consisting of glycerin, polyoxypropylene (1) glycerol and polyoxypropylene (3) glycerol, sorbitol, butylene glycol, propylene glycol, sucrose, and urea and triethanolamine.

The use of oil thickening polymers, such as those listed in EP 0 547 897 A2 to Hewitt, published 23/06/93, incorporated herein by reference, can also be included in the water phase of the emulsions of the present invention.

A variety of additional ingredients can be incorporated into the compositions of the present invention. These materials including, but not limited to, liquid appearance aids, salts and their hydrates and other "filler materials" are listed in U.S. Pat. No. 5,340,492, to Kacher et al., issued Aug. 23, 1994, and U.S. Pat. No. 4,919,934, to Deckner et al., issued Apr. 24, 1990; which is incorporated herein by reference.

Other nonlimiting examples of these additional ingredients include vitamins and derivatives thereof (e.g., ascorbic acid, vitamin E, tocopheryl acetate, and the like); sunscreens; thickening agents (e.g., polyol alkoxy ester, available as Crothix from Croda at levels up to 2% and xanthan gum at levels up to about 2%); preservatives for maintaining the anti-microbial integrity of the compositions; anti-acne medicaments (resorcinol, salicylic acid, and the like); anti-bacterial actives such as triclosan, triclocarban and zinc pyrithione; antioxidants; skin soothing and healing agents such as aloe vera extract, allantoin and the like; chelators and sequestrants; and agents suitable for aesthetic purposes such as fragrances, essential oils, skin sensates, pigments, pearlescent agents (e.g., mica and titanium dioxide), additives to impart a draggy rinse feel (e.g., famed silica), additives to enhance deposition (e.g., maleated soybean oil at levels up to 3%), lakes, colorings, and the like (e.g., clove oil, menthol, camphor, eucalyptus oil, and eugenol).

II. Process for Preparing the Moisturizing Personal Cleansing Emulsion Compositions Herein The elements of the present invention can be applied to any cleansing composition, such as leave-on and rinse-off hair conditioners, hair shampoos, leave-on and rinse-off facial acne preparations, facial milks and conditioners, shower gels, fast foaming and slow foaming facial cleansers, and hand and body lotions. The personal cleansing compositions of the present invention can be prepared using standard procedures using standard materials known in these respective arts. See U.S. Pat. No. 5,641,479, Linares et al, issued Jun. 24, 1997; U.S. Pat. No. 5,599,549, Wivell et al., issued Feb. 4, 1997; U.S. Pat. No. 5,585,104, Ha et al., issued Dec. 17, 1996; U.S. Pat. No. 5,540,852, Kefauver et al., issued Jul. 30, 1996; U.S. Pat. No. 5,510,050, Dunbar et al., issued Apr. 23, 1996; U.S. Pat. No. 5,612,324, Guang Lin et al., issued Mar. 18, 1997; U.S. Pat. No. 5,587,176, Warren et al., issued Dec. 24, 1996; U.S. Pat. No. 5,549,888, Venkateswaran, issued Aug. 27, 1996; and U.S. Pat. No. 5,470,884, Corless et al., issued Nov. 28, 1995; U.S. Pat. No. 5,650,384, Gordon et al., issued Jul. 22, 1997; U.S. Pat. No. 5,607,678, Moore et al., issued Mar. 4, 1997; U.S. Pat. No. 5,624,666, Coffindaffer et al., issued Apr. 29, 1991; U.S. Pat. No. 5,618,524, Bolich, Jr. et al., issued Apr. 8, 1997; U.S. Pat. No. 5,612,301, Inman, issued Mar. 18, 1997; U.S. Pat. No. 5,573,709, Wells, issued Nov. 12, 1996; U.S. Pat. No. 5,482,703, Pings, issued Jan. 9, 1996; U.S. Pat. No. Re. 34,584, Grote et al., Reissued Apr. 12, 1994; U.S. Pat. No. 4,939,179, Cheney et al., issued Jul. 3, 1990; and U.S. Pat. No. 5,607,980, McAtee et al., issued Mar. 4, 1997, all of which are incorporated herein by reference and all of which relate to processes for preparing personal care compositions.

III. Characteristics of the Moisturizing Personal Cleansing Compositions Herein In order to achieve the deposition benefits hereinbefore described and to be consumer-acceptable, it is important that the moisturizing personal cleansing compositions of the present invention have particular rheological characteristics. In particular, the moisturizing personal cleansing compositions of the present invention have a viscosity ranging from about 300 centipoise to about 100,000 centipoise, preferably from about 1,000 centipoise to about 70,000 centipoise, more preferably from about 1,000 centipoise to about 40,000 centipoise, as measured by the Viscosity of the Moisturizing Personal Cleansing Composition Method, hereinafter set forth in the Analytical Methods Section.

The moisturizing personal cleansing compositions of the present invention provide clinically efficacious moisturization benefits to the skin due to increased deposition of the lipophilic skin moisturizing agent. The moisturizing personal cleansing compositions of the present invention have a Lipid Deposition Value of greater than or equal to about 25 micrograms/square centimeter, preferably greater than or equal to about 35 micrograms/square centimeter, and more preferably greater than or equal to about 50 micrograms/square centimeter of lipophilic skin moisturizing agent on the skin as measured by the Deposition of the Lipophilic Skin Moisturizing Agent Method set forth hereinafter in the Analytical Methods section.

Analytical Methods

A number of parameters used to characterize elements of the present invention are quantified by particular experimental analytical procedures. Each of these procedures are described in detail as follows:

1. Viscosity Method for Lipophilic Skin Moisturizing Agents

The Wells-Brookfield Cone/Plate Model DV-II+ Viscometer is used to determine the viscosity of the moisturizing personal cleansing compositions herein. The determination is performed at 25° C. with the 3.0 cm° cone (Spindle CP-52) measuring system with a gap of 0.013 mm between the two small pins on the respective cone and plate. The measurement is performed by injecting 0.5 ml of the sample to be analyzed between the cone and plate and rotating the cone at a set speed of 2 rpm. The resistance to the rotation of the cone produces a torque that is proportional to the shear stress of the liquid sample. The amount of torque is read and computed by the viscometer into absolute poise units based on geometric constants of the cone, the rate of rotation, and the stress related torque.

2. Viscosity of the Moisturizing Personal Cleansing Composition

The Wells-Brookfield Cone/Plate Model DV-II+ Viscometer is used to determine the viscosity of the moisturizing personal cleansing compositions herein. The determination is performed at 25° C. with the 2.4 cm° cone (Spindle CP-41) measuring system with a gap of 0.013 mm between the two small pins on the respective cone and plate. The measurement is performed by injecting 0.5 ml of the sample to be analyzed between the cone and plate and rotating the cone at a set speed of 1 rpm. The resistance to the rotation of the cone produces a torque that is proportional to the shear stress of the liquid sample. The amount of torque is read and computed by the viscometer into absolute centipoise units (mPa-s) based on geometric constants of the cone, the rate of rotation, and the stress related torque.

3. Deposition of the Lipophilic Skin Moisturizing Agent

A. Preparation

The arms are washed with a nonsoap-containing, nonlipid-containing product to reduce background interference as much as possible, then blotted dry. The subject then wets the entire surface of the inner forearm with 95–100° F. tap water for five seconds. One milliliter of the moisturizing personal cleansing composition which contains the lipophilic skin moisturizing agent and weighting oil is applied to the forearm of the subject. The test proctor, wearing a latex glove, gently rubs the product on the skin for 10 seconds to generate lather. The lather is allowed to remain on the forearm for fifteen seconds, followed by a thorough rinse for fifteen seconds with the water flowing from inner elbow to wrist. The subject arm is then patted dry with a paper towel. The subject then allows the arm to "air" dry for 30 seconds.

B. Deposition Protocol-Sebumeter

Deposition of the lipophilic skin moisturizing agent on the skin is measured using a Sebumeter SM810 which is commercially available from Courage and Khazaka GmbH. The Sebumeter measures the amount of lipophilic skin moisturizing agent that has been deposited on the skin via photometry of a special plastic strip, which becomes transparent when it absorbs the lipophilic skin moisturizing agent. The plastic strip is extended over a mirror which is connected to a spring. The measuring head of the device (comprised of spring, mirror and plastic strip) is pressed against the skin for 30 seconds. The Deposition Value ($\mu$g/sq. cm) is indicative of the amount of lipophilic skin moisturizing agent on the skin; the Deposition Value increases with increased amount of lipophilic skin moisturizing agent. The method is insensitive to humidity. Sebumeter readings (3) are taken along the length of the forearm and the Deposition Value ($\mu$g/sq. cm) is defined as the mean of the 3 readings, divided by a conversion factor to translate the sebumeter readings to actual deposition levels in $\mu$g/sq. cm.

The Sebumeter has the following limitations:

1. The Sebumeter tape also detects natural skin lipids. A criterion of this test is that subject's baseline value measured on the Sebumeter, prior to washing, be less than or equal to 3 μg/sq. cm of forearm skin.

2. The Sebumeter like other surface extraction measurements may not measure all the deposited lipophilic skin moisturizing agent; if the skin topography is undulating it is possible that deposited lipophilic skin moisturizing agent may not be extracted by the Sebumeter tape 3. The Sebumeter tape becomes saturated at a Deposition Value of above about 300 μg/sq. cm; so this method can only measure deposition values up to about 300 μsq. cm.

4. Different lipophilic skin moisturizing agents will have different conversion factors. For testing non-petrolatum lipids, a new calibration curve is required.

C. Calibration

To translate the Sebumeter data obtained as hereinbefore described into deposition data, it is necessary to generate a conversion factor. To generate the conversion factor, an extraction is done for each lipid system and the extracted sample is analyzed by gas chromatography. The extraction is done at the same time as the Sebumeter reading and is taken from the same forearm, the extraction procedure is as follows:

1) An open-ended glass cylinder (2 inches in diameter) is placed onto the subject's inner forearm and securely strapped in place.

2) Five ml of extraction solvent is added to the cylinder.

3) The liquid is stirred on the subject's arm for 30 seconds using a blunt-ended glass stirring rod. The full surface area of the enclosed forearm is treated with solvent.

4) The liquid is transferred to a 6 dram vial using a disposable transfer pipet.

5) Steps 2–5 are repeated two times (total of three samples, 15 ml of solvent collected)

The extracted sample is then analyzed by gas chromatography as follows:

APPARATUS

| | |
|---|---|
| Gas Chromatograph | HP 5890 or equivalent equipped with cappillary inlet system and flame ionization detector. |
| Integration System | PEN Turbochrom v4.0 data system, or HP 3396 Series II integrator, or equivalent with peak-grouping capability. |
| Column | DB-5ht, 30 M × 0.32 mm I.D., 0.10 μm film thickness, J&W Scientific cat. no. 123-5731. |
| Analytical Balance | Capable of weighting to 0.0001 g. |
| Pipet | 1 ml, Class A. |
| Volumetric Flask | 1000 ml, 100 ml, glass stoppered. |
| Glass Syringe | 100 μl capacity |
| Autosampler Vials | With crimp-top caps |
| Dry Bath | Regulated at 80–85 ° C. |
| Pipettor | Ependoff Repeator with 12.5 ml reservoir |
| Stir Plate and Stir Bars | Teflin-coated stir bars |

REAGENTS

| | |
|---|---|
| Heptane | ACS grade. |
| Squalane | Aldrich cat. no. 23,431-1 or equivalent. |
| Lipid Standard | Lot of lipid used in the test product. |

GC CONDITIONS

| | |
|---|---|
| Carrier Gas | Helium UHP grade or regular grade helium purified through a dry tube and an oxygen scrubber. Flow pressure regulated at 25 psi with 25 ml/min split. |
| Injection Mode | Splitless |
| Injection Volume | 2 μl |
| Injector Temperature | 310° C. |
| Oven Temperature Program | 100° C. for 0 minutes @ 10° C./min. to 350° C.; hold for 6 min. |
| Detector Temperature | 350° C. |
| Hydrogen and Air Flows | Optimized for gas chromatograph used. |
| Bunching Factor | 2 |

SOLUTIONS

| | |
|---|---|
| Internal Standard Solution | Into a clean, dry 100 ml volumetric flask, analytically weight 0.1 g of squalane, recording weight to nearest 0.0002 g. Dilute to volume with heptane, stopper and stir to dissolve. (A1:1000 dilution of this solution can be used as the extraction solvent when generating samples.) |
| Lipid Stock Solution | Into a clean, dry 100 ml volumetric flask, analytically weight 0.5 gram of lipid standard, recording weight to nearest 0.0002 g. Dilute to volume with heptane, stopper and stir to mix. |
| Lipid Working Standards | Label three autosampler vials as follows: "100 μg," "300 μg" and "500 μg." Using the glass syringe, transfer 15 μl of internal standard solution into each vial. Rinse syringe well with heptane, then use it to transfer the following amounts of lipid stock solution to the vials: |

| Std. | Vol. Stock Soln. (μl) |
|---|---|
| 100 μg | 20 |
| 300 μg | 60 |
| 500 μg | 100 |

Dilute to approx. 0.5 ml with heptane, then cap and shake to mix.

OPERATION

| | |
|---|---|
| 1. Calibration | Run each standard under the above conditions. Select the 10–14 largest peaks frorn the calibration run and create a peak group within the calibration of the method. Assign the amount of lipid in the standard to the group for each calibration level. Plot the area ratio on the y-axis. Do not force the line through the origin or include the origin. The r2 value should be at least 0.9990. Check calibration every ten or twelve samples and at the end of the sample run. |
| 2. Sample Analysis | Evaporate samples to dryness under a stream of dry nitrogen. Reconstitute in 0.5 ml heptane. Cap tightly and place on dry bath for 5 minutes; shake to dissolve completely.Transfer to autosampler vials and analyze on calibrated instrument with the proper ISTD amount entered. Important: Because the baseline is cluttered, manually check each result file for correct peak identification. |

The GC data is then plotted on a curve versus the Sebumeter data. The slope of the curve is the conversion factor. The conversion factor for petrolatum is 0.56.

4. Droplet Size Measurement for Moisturizing Phase Droplets

Light microscopy is used as the supplemental droplet size measurement technique to measure the size of the moisturizing phase droplets. In this technique, the product is viewed under very low magnification (<10×) between a plate and coverslip and moisturizing phase droplet sizes are estimated via a micrometer. The droplet size of the total population is determined, and a weighted average is calculated.

EXAMPLES

The following shower gel compositions are nonlimiting examples of the aerosol ersonal cleansing compositions of the present invention.

| Ingredients | Wt % A | Wt % B | Wt % C | Wt % D | Wt % E |
|---|---|---|---|---|---|
| Ammonium Alkyl Ethoxylated-3 Sulfonate ($AE_3S$) | 5.13 | 5.13 | 5.13 | 5.13 | 5.13 |
| Ammonium Lauryl Sulfate (ALS) | 1.50 | 1.50 | 1.50 | 1.50 | 1.50 |
| Lauroamphoacetate | 1.43 | 1.43 | 1.43 | 1.43 | 1.43 |
| Trihydroxystearin | 0.50 | 0.50 | 0.50 | 0.50 | 0.50 |
| Lauryl Alcohol | 0.25 | 0.25 | 0.25 | 0.25 | 0.25 |
| Polymer JR 30M | 0.30 | 0.30 | 0.30 | 0.30 | 0.30 |
| Petrolatum | 5.00 | 5.00 | 5.00 | 5.00 | 5.00 |
| Soybean Oil | 9.00 | 10.00 | 14.00 | 5.00 | 7.50 |
| Brominated Soybean Oil | 0.00 | 0.00 | 0.00 | 10.00 | 7.50 |
| Citric Acid | 1.00 | 1.00 | 1.00 | 1.00 | 1.00 |
| Preservative | 0.60 | 0.60 | 0.60 | 0.60 | 0.60 |
| Perfume | 0.80 | 0.80 | 0.80 | 0.80 | 0.80 |
| Water | QS | QS | QS | QS | QS |

| Ingredients | Wt % F | Wt % G | Wt % H | Wt % I | Wt % J |
|---|---|---|---|---|---|
| Ammonium Alkyl Ethoxylated-3 Sulfonate ($AE_3S$) | 5.13 | 5.13 | 5.13 | 4.73 | 5.13 |
| Ammonium Lauryl Sulfate (ALS) | 1.50 | 1.50 | 1.50 | 0.00 | 1.50 |
| Lauroamphoacetate | 1.43 | 0.00 | 0.00 | 5.25 | 0.00 |
| Cocamidopropyl Betaine | 0.00 | 2.00 | 0.00 | 0.00 | 0.00 |
| Sodium Cocoyl Isethionate | 0.00 | 0.00 | 2.00 | 0.00 | 0.00 |
| Sodium Lauroyl Lactylate | 0.00 | 0.00 | 0.00 | 0.00 | 2.00 |
| Sodium Citrate | 0.00 | 0.00 | 0.00 | 1.25 | 0.00 |
| Trihydroxystearin | 0.50 | 0.50 | 0.50 | 0.00 | 0.50 |
| Lauryl Alcohol | 0.25 | 0.25 | 0.25 | 0.00 | 0.25 |
| Glycerin | 0.00 | 2.00 | 2.00 | 3.00 | 0.00 |
| Polymer JR 30M | 0.30 | 0.30 | 0.30 | 0.40 | 0.30 |
| Softigen 767 | 0.00 | 0.00 | 0.00 | 3.40 | 0.00 |
| Ceraphyl GA-D | 0.00 | 0.00 | 0.00 | 1.50 | 0.00 |
| PK1218 Fatty Acid | 0.00 | 0.00 | 0.00 | 2.43 | 0.00 |
| Monamid CMA | 0.00 | 0.00 | 0.00 | 3.28 | 0.00 |
| Petrolatum | 5.00 | 5.00 | 5.00 | 0.00 | 5.00 |
| Soybean Oil | 7.50 | 7.50 | 7.50 | 0.00 | 7.50 |
| Brominated Soybean Oil | 7.50 | 7.50 | 7.50 | 0.00 | 7.50 |
| Citric Acid | 1.00 | 0.50 | 0.50 | 1.00 | 1.00 |
| Preservative | 0.60 | 0.60 | 0.60 | 0.60 | 0.60 |
| Perfume | 0.80 | 0.80 | 0.80 | 0.80 | 0.80 |
| Water | QS | QS | QS | QS | QS |

| Aerosol Packing | |
|---|---|
| Examples A–J | 85%–97% |
| Propellant mixture of 85% isopentane/15% isobutane | 3%–15% |

Making Procedure

The making procedure consists of the making of 2 premixes, a moisturizing phase premix and a polymer premix, in addition to the main mix. The critical step in this process is insuring that the lipid premix is added to the main mix without excessive agitation.

The $AE_3S$ and ALS are added first to the main mix tank. Citric acid is then added. Then the remainder of the surfactants are added. Add the trihydroxystearin, lauryl alcohol, and all required water, less 10% for the polymer premix. Heat the surfactant mixture to 160° F.

Prepare a polymer premix, by mixing 10%, by weight of the total composition batch weight, of water and the JR 30M polymer. Mix well. When main mix tank ingredients reach 160° F., add polymer premix. Heat main mix to 190° F.

Start the moisturizing phase premix when the polymer premix addition is completed. It is imperative that the main mix is well underway prior to starting the moisturizing phase premix. Add all of the oil components, including the weighting oil to premix tank. Heat the premix until the temperature reaches 130° F. to 140° F. When all of the oil components are thoroughly mixed, discontinue heating.

Cool the main mix. When the main mix has reached a target temperature of 140° F., slowly add the moisturizing phase premix. Slowly mix batch until the oil phase is thoroughly mixed with the main mix. Add the remaining minor ingredients, slowly cool the batch until it reaches a temperature of 80° F.–100° F.

The foaming compositions of examples A–J are then packed into the appropriate aerosol container. The aerosol package options include: aerosol metal containers, bag-in-a-bottle, bag-in-a can, etc. The type package chosen is dependent on the desired product form. The containers are pressurized with hydrocarbon propellant.

What is claimed is:

1. A pressurized personal cleansing composition comprising:
   a) from about 85% to about 95%, by weight of the composition, of a neat cleansing lotion comprising:
      i) from about 0.5% to about 30%, by weight of the neat cleansing lotion, of a lathering surfactant;
      ii) from about 5% to about 40%, by weight of the neat cleansing lotion, of a lipophilic skin moisturizing agent;
      iii) from about 0.1% to about 10%, by weight of the neat cleansing lotion, of a stabilizer; and
      iv) from about 35% to about 90%, by weight of the neat cleansing lotion, of water; and
   b) from about 3% to about 15%, by weight of the composition, of a hydrocarbon propellant having a vapor pressure of from about 3 psig to about 15 psig at 70° F., wherein at least a portion of the hydrocarbon propellant is solubilized in the lipophilic skin moisturizing agent; wherein the composition is adapted to apply the lipophilic skin moisturizing agent in an average droplet size of from about 10 to about 350 microns in diameter.

2. The pressurized personal cleansing composition according to claim 1, wherein the neat cleansing lotion comprises from about 2% to about 20%, by weight of the neat cleansing lotion, of the lathering surfactant.

3. The pressurized personal cleansing composition according to claim 1, wherein neat cleansing lotion comprises from about 5% to about 10%, by weight of the neat cleansing lotion, of the lathering surfactant.

4. The pressurized personal cleansing composition according to claim 1, wherein the composition is packaged in a container and adapted for dispensing in aerosol form.

5. The pressurized personal cleansing composition according to claim 4, wherein the lathering surfactant comprises anionic surfactant selected from the group consisting of acyl isethionates, acyl sarcosinates, alkylglycerylether sulfonates, acyl lactylate, methylacyl taurates, paraffin sulfonates, linear alkyl benzene sulfonates, N-acyl glutamates, alkyl sulfosuccinates, alpha sulfo fatty acid esters, alkyl ether carboxylates, alkyl sulfates, alkyl phosphate esters, ethoxylated alkyl phosphates esters, alpha olefin sulphates, alkyl ether sulfates containing 1 to 12 ethoxy groups, and mixtures thereof, wherein the anionic surfactant contains $C_8$ to $C_{22}$ alkyl chains and wherein the anionic surfactant has a counterion selected from the group consisting of Na, K, $NH_4$ and $N(CH_2CH_2OH)_3$.

6. The pressurized personal cleansing composition according to claim 4, wherein the lathering surfactant comprises from about 1 to about 10 parts, by weight of the neat cleansing lotion, of an amphoteric surfactant selected from the group consisting of alkyl-ampho mono- and di-acetates, alkyl dimethyl amine oxides, alkyl betaines, alkyl sultaines, alkyl amidopropyl betaines, alkyl amidopropyl hydroxysultaines, and mixtures thereof, wherein the amphoteric surfactant contains $C_8$ to $C_{22}$ alkyl chains.

7. The pressurized personal cleansing composition according to claim 4, wherein the lathering surfactant comprises from about 1% to about 15%, by weight of the neat cleansing lotion, of a nonionic surfactant selected from the group consisting of alkyl glucose amides, alkyl glucose esters, polyoxyethylene amides, fatty alkane amides, alkyl amine oxides, alkyl polyglucosides, polyoxyethylene alkyl phenols, polyoxyethylene esters of fatty acids, ethylene oxide/propylene oxide copolymers, sorbitan esters and alcohol esters, and mixtures thereof.

8. The pressurized personal cleansing composition according to claim 4, wherein the lathering surfactant comprises from about 0.5% to about 6%, by weight of the neat cleansing lotion, of a cationic surfactant selected from the group consisting of stearylalkonium chloride, stearyltrimonium chloride, di-stearyl-dimonium chloride, and mixtures thereof.

9. The pressurized personal cleansing composition according to claim 1, wherein the neat cleansing lotion comprises from about 5% to about 25%, by weight of the neat cleansing lotion, of the lipophilic skin moisturizing agent.

10. The pressurized personal cleansing composition according to claim 1, wherein the lipophilic skin moisturizing agent is selected from the group consisting of hydrocarbon oils and waxes, silicones, di- and tri-glycerides, acetoglyceride esters, lanolin and lanolin derivatives, and mixtures thereof.

11. The pressurized personal cleansing composition according to claim 1, wherein the average droplet size of the lipophilic skin moisturizing agent is from about 50 to about 200 microns in diameter.

12. The pressurized personal cleansing composition according to claim 1, wherein the stabilizer comprises a) crystalline, hydroxy-containing stabilizers selected from the group consisting of:

i) 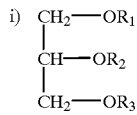

wherein

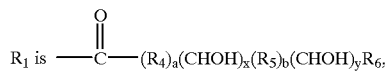

$R_2$ is $R_1$ or H,
$R_3$ is $R_1$ or H,
$R_4$ is $C_{1-20}$ alkyl,
$R_5$ is $C_{1-20}$ alkyl,
$R_6$ is $C_{1-20}$ alkyl or H,
a and b are individually 0 or 1, and
$R_4$, $R_5$ and $R_6$ combined contain 10 to 22 carbon atoms,
and wherein $1 \leq x+y \leq 4$;

ii) 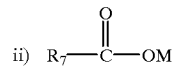

wherein $R_7$ is $-R_4(CHOH)_xR_5(CHOH)_yR_6$ and M is $Na^+$, $K^+$, $Mg^{++}$, or H; and iii) mixtures thereof;

b) $C_{10}$–$C_{22}$ ethylene glycol fatty acid ester;

c) amorphous silica;

d) smectite clay selected from the group consisting of bentonite, hectorite and mixtures thereof; and e) mixtures thereof.

13. The pressurized personal cleansing composition according to claim 1, wherein the hydrocarbon propellant comprises about 85% isopentane and about 15% isobutane.

14. The pressurized personal cleansing composition according to claim 1, wherein the hydrocarbon propellant comprises from about 5% to about 12% by weight of the composition.

15. A pressurized personal cleansing composition comprising:

I) from about 85% to about 95%, by weight of the composition, of a neat cleansing lotion comprising:
  A) from about 0.5% to about 30%, by weight of the neat cleansing lotion, of a lathering surfactant;
  B) from about 5% to about 40%, by weight of the neat cleansing lotion, of a lipophilic skin moisturizing agent;
  C) from about 0.1% to about 10%, by weight of the neat cleansing lotion, of a stabilizer selected from the group consisting of:
    a) crystalline, hydroxy-containing stabilizers selected from the group consisting of:

i) 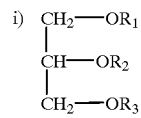

wherein

$R_2$ is $R_1$ or H,
$R_3$ is $R_1$ or H,
$R_4$ is $C_{1-20}$ alkyl,
$R_5$ is $C_{1-20}$ alkyl,
$R_6$ is $C_{1-20}$ alkyl or H,
a and b are individually 0 or 1, and
$R_4$, $R_5$ and $R_6$ combined contain 10 to 22 carbon atoms,
and wherein $1 \leq x+y \leq 4$;

ii) 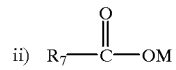

wherein $R_7$ is —$R_4$(CHOH)$_x$$R_5$(CHOH)$_y$$R_6$ and M is Na$^+$, K$^+$, Mg$^{++}$, or H; and iii) mixtures thereof;

b) $C_{10}$–$C_{22}$ ethylene glycol fatty acid ester;

c) amorphous silica;

d) smectite clay selected from the group consisting of bentonite, hectorite and mixtures thereof; and e) mixtures thereof;

D) from about 35% to about 90%, by weight of the neat cleansing lotion, of water;

II) from about 3% to about 15%, by weight of the composition, of a hydrocarbon propellant comprising a mixture of isobutane and isopentane, wherein the hydrocarbon propellant has a vapor pressure of from about 3 psig to about 15 psig at 70° F. and at least a portion of the hydrocarbon propellant is solubilized in the lipophilic skin moisturizing agent; wherein the composition is adapted to apply the lipophilic skin moisturizing agent in an average droplet size of from about 10 to about 350 microns in diameter.

16. The pressurized personal cleansing composition according to claim 15, wherein the hydrocarbon propellant comprises about 85% isopentane and about 15% isobutane.

17. The pressurized personal cleansing composition according to claim 16, wherein the lathering surfactant comprises an anionic surfactant.

18. The pressurized personal cleansing composition according to claim 17, wherein the anionic surfactant is selected from the group consisting of acyl isethionates, acyl sarcosinates, alkylglycerylether sulfonates, acyl lactylate, methylacyl taurates, paraffin sulfonates, linear alkyl benzene sulfonates, N-acyl glutamates, alkyl sulfosuccinates, alpha sulfo fatty acid esters, alkyl ether carboxylates, alkyl sulfates, alkyl phosphate esters, ethoxylated alkyl phosphates esters, alpha olefin sulphates, alkyl ether sulfates containing 1 to 12 ethoxy groups, and mixtures thereof, wherein the anionic surfactant contains $C_8$ to $C_{22}$ alkyl chains and wherein the anionic surfactant has a counterion selected from the group consisting of Na, K, NH$_4$, and N(CH$_2$CH$_2$OH)$_3$.

19. The pressurized personal cleansing composition according to claim 15, wherein the average droplet size of the lipophilic skin moisturizing agent is from about 50 to about 200 microns in diameter.

20. The pressurized personal cleansing composition according to claim 15, wherein the hydrocarbon propellant comprises from about 5% to about 12% by weight of the composition.

* * * * *